United States Patent [19]

Wei et al.

[11] Patent Number: 4,481,191

[45] Date of Patent: Nov. 6, 1984

[54] METHOD FOR CONTROLLING BLOOD PRESSURE

[75] Inventors: Edward T. Wei, El Cerrito; Nancy M. Lee, San Francisco; Jaw-Kang Chang, San Carlos, all of Calif.

[73] Assignee: The Regents of the University of California, Berkeley, Calif.

[21] Appl. No.: 480,691

[22] Filed: Mar. 30, 1983

[51] Int. Cl.$^3$ .................... A61K 37/00; C07C 103/52
[52] U.S. Cl. ............................ 424/177; 260/112.5 E
[58] Field of Search .................. 260/112.5 E; 424/177

[56] References Cited

U.S. PATENT DOCUMENTS

| Re. 30,496 | 1/1981 | Failli et al. | 260/112.5 R |
|---|---|---|---|
| 3,299,036 | 1/1967 | Boissonnas et al. | 260/112.5 R |
| 3,299,037 | 1/1967 | Boissonnas et al. | 260/112.5 R |
| 3,558,590 | 1/1971 | Cort et al. | 260/112.5 R |
| 3,980,631 | 9/1976 | Prochazka et al. | 260/112.5 R |
| 4,163,011 | 7/1979 | Orts | 260/112.5 R |
| 4,215,111 | 7/1980 | Goldstein et al. | 260/112.5 R |
| 4,215,112 | 7/1980 | Goldstein et al. | 260/112.5 R |
| 4,361,553 | 11/1982 | Loh et al. | 424/177 |
| 4,374,829 | 2/1983 | Harris et al. | 424/177 |

OTHER PUBLICATIONS

Kiang et al., *Exp. Ther.* (1983), "Tolerance to Morphine Bradycardia in the Rat."
Wei et al., *Life Sciences*, vol. 26, pp. 1517-1522 (1980), "Cardiovascular Effects of Peptides Related to the Enkephalins and-Casomorphin."
Kiang et al., *Amer. Soc. Phar. Exp. Thera.*, 1982 FASEB Abstract Form, "Tolerance Development to Morphine Bradycardia in the Rat and its Modification by Dynorphin (1-13) and Leucine-Enkephalin."
Sapru et al., *Jour. Phar. & Exp. Ther.* 217:228-234 (1981), "Stimulation of Pulmonary J Receptors by an Enkephalin-Analog."
Abstract of *Life Sciences*, vol. 31, Feurenstein and Faden.
Feurenstein and Faden, *Life Sciences*, vol. 31, pp. 2197-2200, (Nov., 1982).
Title of Poster Talk, Feurenstein and Faden, International Narcotic Research Conference, (Jun. 16, 1982).
C. E. Baker, "Physicians' Desk Reference," (1981), p. 1573.
Computer Printout.

*Primary Examiner*—Delbert R. Phillips
*Attorney, Agent, or Firm*—Majestic, Gallagher, Parsons & Siebert

[57] ABSTRACT

A method is provided for treating high blood pressure and disturbances of cardiac function by administering a therapeutically effective dosage of dynorphin-related opioid peptides, such as dynorphin(1-13) and dynorphin(1-10) amide, having at least ten amino acids linked sequentially by peptide bonds and with the five amino acids from the N-terminal end being the same as, or mimicking, Leu-enkephalin. Administration may be over a period of time, as for individuals with chronic high blood pressure, and may be by dispensing the medicament in aerosol form.

7 Claims, 3 Drawing Figures

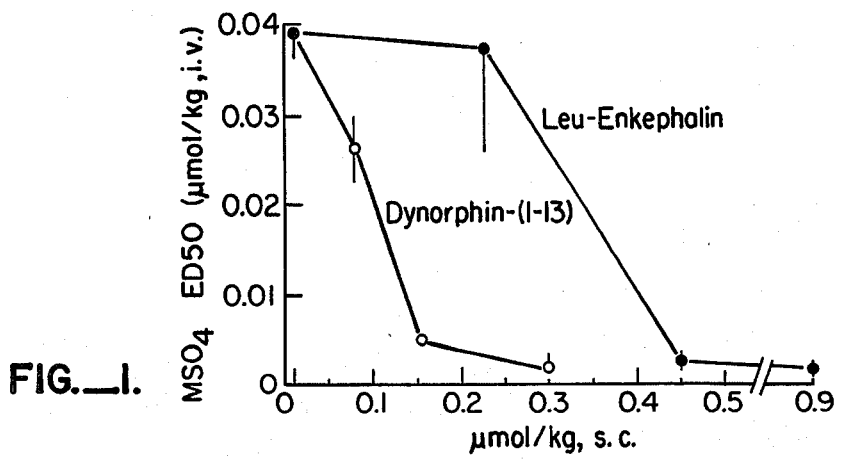
FIG._1.
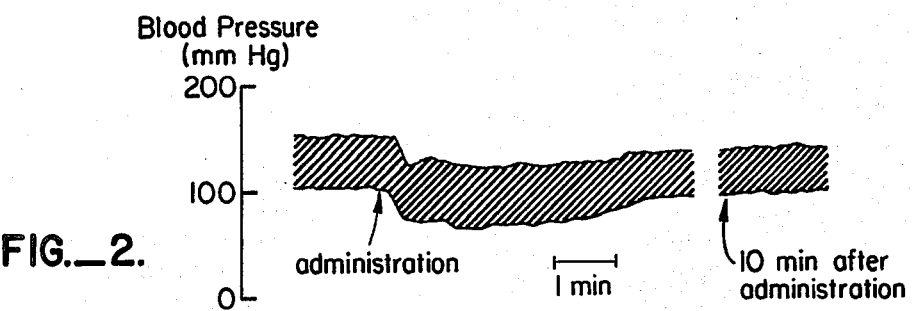
FIG._2.
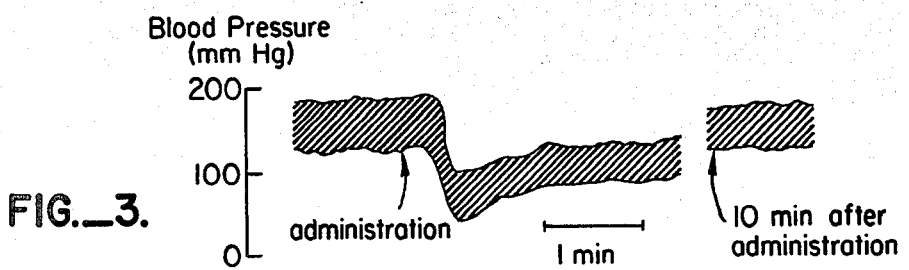
FIG._3.

METHOD FOR CONTROLLING BLOOD PRESSURE

This invention was made with Government support under Grant No. DA 00091 awarded by the Department of Health and Human Services. The Government has certain rights in this invention.

DESCRIPTION

1. Field of the Invention

The present invention generally relates to dynorphin and dynorphin analogs, and more particularly to uses thereof in treating high blood pressure.

BACKGROUND OF THE INVENTION

The various known antihypertensive medications (i.e., drugs which lower blood pressure) can be generally classed by their in vivo modes of action.

One class of drugs called, collectively, the veratrum alkaloids, is effective in lowering blood pressure because the compounds are able to "fool" the brain into thinking that blood pressure is high. The brain then reflexly lowers blood pressure. Although effective for lowering blood pressure, the veratrum alkaloids have adverse side effects and hence their use as antihypertensive medication has become obsolete.

The presently used drugs for antihypertension generally either act within the brain to inhibit neurons or to interfere with peripheral nerve endings and the adjacent blood vessels. An example of the former are clonidine-type drugs. An example of the latter is guanethidine.

Dynorphin is a porcine pituitary peptide which contains seventeen amino acids and has potent agonist properties in guinea pig ileum and mouse vas deferens. Both dynorphin(1-13) and dynorphin(1-17) have been sequenced and synthesized. The synthetic dynorphin(1-13) product has been found to be as potent in bioassays as the naturally occuring peptide, but has been shown to be relatively weak in producing analgesia in studies with mice.

It has been reported that dynorphin(1-13), but not the shorter fragment dynorphin(1-9), has significant effects on opiate and beta-endorphin-induced analgesia in naive animals. The studies have suggested that dynorphin(1-13) may interact with other analgesic opioids. Thus, it has been shown that dynorphin(1-13) appears to interact with morphine to significantly modify the analgesia produced by morphine in naive animals. Therapeutic uses of dynorphin, particularly dynorphin(1-13), for hosts tolerant to narcotic analgesics are described in U.S. Pat. No. 4,361,553, inventors Horace H. Loh and Nancy M. Lee, issued Nov. 30, 1982. Use of dynorphin(1-10) amide to potentiate narcotic induced analgesia in tolerant hosts is described in pending U.S. patent application Ser. No. 387,005, filed June 10, 1982, entitled "Dynorphin Amide Analogs", inventors Lee, et al.

The first thirteen amino acids of dynorphin, or dynorphin(1-13), have the sequence:

pertensive drugs such as the veratrum alkaloids, clonidine and sympatholytic type drugs.

SUMMARY OF THE INVENTION

In one aspect of the present invention, a method for treating high blood pressure and disturbances of cardiac function is provided by administering a dynorphin-related compound in a therapeutically effective dosage. Administration may be oral, by injection, or intranasal, and preferred compounds for use in the inventive method are dynorphin(1-13) and dynorphin(1-10) amide.

In another aspect of the present invention, an apparatus is provided which is useful for antihypertensive treatment and cardiac function disturbances, and comprises a medicament including a dynorphin-related compound and a means for dispensing the medicament in an aerosol form.

BRIEF DESCRIPTION OF THE DRAWINGS

In the drawings

FIG. 1 plots a median effective dose of morphine sulfate for producing bradycardia after administration of different doses of dynorphin(1-13) or Leu-enkephalin;

FIG. 2 plots the blood pressure of one animal receiving a dose of dynorphin(1-10) amide; and, FIG. 3 plots the blood pressure of another animal receiving a dose of dynorphin(1-10) amide.

DETAILED DESCRIPTION OF THE PREFERRED EMBODIMENTS

The autonomic nervous system is a critical monitoring network for the maintenance of a variety of physiological functions. Visceral afferent receptors are sensory nerve endings that detect chemical information in the blood and visceral organs. This information is then conveyed to the brain where integration of the information evokes reflexes that tend to adjust the chemical or physiological systems of the body back to equilibrium. Among these visceral afferent nerves are peripheral C-fiber afferents, which are small, slow-conducting, non-myelinated fibers that carry nerve signals to the brain from the periphery. Fibers that mediate a fall in heart rate and blood pressure are most likely located in the cardiopulmonary tree (i.e., heart, blood vessels and lung tissues).

It is believed peripheral nerve endings present in the heart and blood vessels are important for the control of blood pressure. For example, that when a normal individual's blood pressure goes up, the afferent signals are increased and reflexes are activated so that blood pools in the lower extremities, resulting in a fall in blood pressure.

With age, the elasticity of the blood vessels decline, so that changes in pressure are detected less readily by the nerve endings. One consequence when reflexes are less operational is a gradual rise in blood pressure.

Opioid peptides are found in the circulatory system,

TYR—GLY—GLY—PHE—LEU—ARG—ARG—ILE—ARG—PRO—LYS—LEU—LYS.
 1     2     3     4     5     6     7     8     9    10    11    12    13

The N-terminal end contains Leu-enkephalin (those amino acids numbered 1-5), followed by the C-terminal extension (those amino acids numbered 6-13). Dynorphin's structure is quite different from known antihypertensive drugs such as the veratrum alkaloids, clonidine and sympatholytic type drugs.

presumably from sources in the pituitary (Imura et al., *Ann Rev. Physiol.* 43: 265-278, (1981)), adrenal medulla (Viveros et al, *Adv. Biochem. Psychopharmacol.* 22: 191-204 (1980)), heart (Lang et al., *Life Sci.* 32: 399-406

(1983)), and gut (Elde et al., *Neuroscience* 1: 349-357 (1976); Polak et al., *Lancet* 1: 972-974 (1977); Alumets et al., *Histochem* 56: 187-196 (1978)).

A prevailing theory is that most actions of opioid drugs are within the central nervous system (that is, inside the brain or spinal cord). However, evidence that endogenous opioid peptides appear to condition the sensitivity of the peripheral nerves to stimuli that affect heart rate and blood pressure has been found, and it is believed that circulating opioid peptides, under normal conditions, are operating to control the sensitivity of these peripheral sites of the autonomic nervous system to such endogenous substances.

It has been further discovered the endogenous levels of opioid peptides are important in controlling the resting level of visceral afferent activity. This means that the autonomic nervous system is constantly sampling the blood stream for opioid peptides and information is being fed back into the brain for reflex control. The system appears to operate as a fine-tuned control network for visceral function.

Endogenous enkephalins and/or endorphins appear to function as signals that switch on and off physiological functions, particularly signals to the peripheral nerve endings that affect heart rate and blood pressure. Several short-chain opioid peptides related to enkephalins and to beta-casomorphin have been studied, and bioassays based on heart rate have been described. (Wei et al., *Life Sci.* 26: 1517-1522 (1980)).

The present invention is a method for modifying the autonomic nervous system by administering a therapeutic agent that amplifies and maintains the intensity of endogenous opioid peptides. More particularly, administering a therapeutically effective dosage of a suitable therapeutic agent is useful in treating high blood pressure and disturbances of cardiac function, such as arrhythmias and cardiac pain. A mode of action for the dynorphin-related compounds may be by increasing the sensitivitiy of visceral afferent receptors.

Suitable therapeutic agents administered in a method for treating high blood pressure and cardiac disturbances according to the present invention are dynorphin-related opioid peptides.

The dynorphin-related, opioid peptides for practice of the present invention have at least ten amino acids linked sequentially by peptide bonds, with the five amino acids from the N-terminal end being the same as, or mimicking, Leu-enkephalin.

Suitable dynorphin-related opioid peptides have the structure illustrated by Formula I, below.

alkyl, a benzylic group (substituted or unsubstituted), one of $R_{11}$ and $R_{12}$ may be a nitrogen containing moiety such as hydrazide and the other hydrogen, or one of $R_{11}$ and $R_{12}$ may be a basic or neutral amino acid or a basic or neutral di-, tri-, or poly-peptide and the other hydrogen or an alkyl group; $R_3$–$R_9$ are hydrogen or an alkyl group of not more than about four carbons (branched or unbranched), more preferably methyl or ethyl; and, the sequential amino acids are as follows:

$AA^1$ may be tyrosine, m-tyrosine or dopa (d or l form), more preferably tyrosine;

$AA^2$ and $AA^3$ may be glycine or other neutral amino acids in either the d or l form (e.g., serine, threonine, cysteine, tyrosine, asparagine, methionine and glutamine) or alpha-amino isobutyric acid (AIB), more preferably glycine;

$AA^4$ may be phenylalanine, alpha-alkylated phenyl alanine (such as alpha-methyl phenylalanine), phenylalanine with a para-substituted electron withdrawing group, such as a halogen or nitro group, for example p-halo-phenylalanine, or tyrosine, more preferably phenylalanine;

$AA^5$ may be leucine, isoleucine or valine, more preferably leucine;

$AA^6$ and $AA^7$ may be a basic acid in either the d or l form (e.g., arginine, lysine or histidine), homoarginine or ornithine, more preferably arginine;

$AA^8$ may be neutral or basic amino acids in the d or l form, leucine or isoleucine, more preferably tyrosine, isoleucine, or lysine;

$AA^9$ may be a basic amino acid in either the d or l form, homoarginine, ornithine, or proline, more preferably arginine or proline; and $AA^{10}$ may be a basic amino acid in either the d or l form, proline, or a proline analog (such as thioproline, 3,4-dehydroproline, 4-hydroxyproline, or pipecolic acid), more preferalby proline or lysine.

Where $R_{11}$ or $R_{12}$ is a di-,tri-, or polypeptide, then a particularly preferred sequence therefor is -LYS, -LYS-LEU, or -LYS-LEU-LYS. Particularly preferred dynorphin-related, or dynorphin analogs, are:

TYR—GLY—GLY—PHE—LEU—ARG—ARG—ILE—ARG—PRO
 1    2    3    4    5    6    7    8    9   10 where the carbonyl carbon at the proline terminus is amidated (sometimes referred to herein as "dynorphin(1-10) amide"); and TYR—GLY—GLY—PHE—LEU—ARG—ARG—LYS—ARG—PRO—LYS—LEU—LYS
 1    2    3    4    5    6    7    8    9   10   11   12   13

(sometimes referred to herein as "dynorphin(1-13)").

Administration of dynorphin analogs in accordance with the present invention is believed to function by enhancing the sensitivity of visceral afferents in the heart and lung to the circulation of endogenous opioid peptides, such as leucine-enkephalin.

FORMULA I

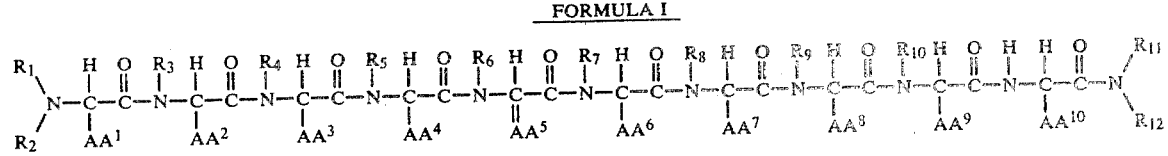

where $R_1$ and $R_2$ are hydrogen, alkyl, allyl, or acyl (such as formyl or acetyl); $R_{11}$ and $R_{12}$ are hydrogen, As described by Wei, et al. *Life Sciences,* supra, endogenous, short-chain opioid peptides, such as methionine-enkephalin, leucine-enkephalin and beta-endorphin, produce a lowering of heart rate and blood pressure when administered intravenously (i.v.). The median effective doses (ED50) for methionine-enkephalin, leucine-enkephalin and beta-endorphin being 1.3, 1.5 and 0.07 μmol/kg, respectively. The qualitative features of this effect, namely the immediate, short-lasting fall in heart rate and blood pressure, are essentially identical to that for morphine at about 15 microgram/kg i.v. (e.g., a dose at least 100 times lower than that which produces analgesia and respiratory depression). The i.v. administration of Leu-enkephalin and the in vivo response thereto exemplifies the normal animal's response to endogenous, circulating opioid peptides such as Leu-enkephalin, met-enkephalin and beta-endorphin. In the disease state, such as where elasticity of the blood vessels has declined, or where inappropriate endogenous secretion has desensitized the nerve endings (a "tolerant" state), such a response will tend to be attenuated, or damped, as the visceral afferent receptors become less sensitive to the stimulus of circulating opioid peptides.

Theoretically, endogenous opioid peptides released during periodic or short-term stress can desensitize these nerve endings. In the desensitized, or "tolerant", state, a decreased level of peripheral signals enter the brain. The brain may then raise the blood pressure level in order to "hear" the periphery more clearly.

Turning to FIG. 1, the ordinate thereof represents the ED50 of morphine sulfate for producing a greater than 10% fall in heart rate in rats, and serves as an index of the sensitivity of the animal to the drug. Morphine sulfate functions as a "challenge" drug for producing bradycardia, and is a traditional standard for comparison. Lower ED50 values mean that the visceral afferent receptors are more sensitive. The abscissa of FIG. 1 represents doses of dynorphin(1-13) and Leu-enkephalin, respectively, in units of micromoles per kg body weight administered subcutaneously 30 minutes before testing with morphine sulfate. The data plotted in FIG. 1 show that prior administration of Leu-enkephalin or dynorphin(1-13) enhances sensitivity, but that dynorphin(1-13) is about 5 times more active than Leu-enkephalin.

FIGS. 2 and 3 illustrate the changes in blood pressure following administration of a dynorphin(1-10) amide, with the animal of FIG. 2 being a 267 gram rat receiving 0.1 mg/kg of body weight, intravenously, and the animal of FIG. 3 being a 4.7 kg cat receiving 0.17 mg/kg body weight administered into the left ventricle of the heart. The animals were anesthetized prior to the administering.

Thus, as illustrated by FIGS. 2 and 3, administration of dynorphin-related peptides in sufficient, or therapeutically effective, amounts produce a pronounced drop in blood pressure. Administration may be over a period of time as an antihypertensive agent (for individuals with chronic high blood pressure) or may be on a short-term basis for crisis situations such as in certain forms of cardiac arrhythmias, particularly ventricular tachycardia and fibrillation. Increased vagal action may be desirable in certain forms of cardiac arrhythmias such as ventricular tachycardia and fibrillation. Administration of dynorphin-related compounds, such as dynorphin(1-13), can increase vagal activity and counteract cardiac arrhythmias arising from sympathetic activity.

It is contemplated that dynorphin, dynorphin analogs and related peptides may also be useful in applications to relieve cardiac pain, for example, in heart attacks and in angina. Cardiac pain arising from myocardial infarcts (heart attacks) or angina (decreased oxygenation of heart muscle) is believed to be due to stimulation of cardiac C-fiber afferents in the sympathetic nerve. Dynorphin-related compounds may be used to accelerate the rate of desensitization, which results in fewer messages to the brain concerning the state of the heart. Although dynorphin-related compounds sensitize in the short-term, in the longer term such opioid peptides act to desensitize because the short-term sensitization accelerates the development of desensitization.

Use of dynorphin-related compounds, particularly the preferred dynorphin(1-13) and dynorphin(1-10) amide may be administered as antihypertensive agents on a daily basis (for chronic cases) in doses from about 10 to 30 mg/70 kg body weight. Administration can be oral, intranasal, percutaneous, or by injection. That is, the dynorphin-related compounds can be dispensed as an aerosol into the nasal turbinates or given sublingually, which avoids degradation of the therapeutic compounds by the digestive tract and by the liver after it is absorbed into the abdominal circulation. A particularly preferred means of administration is use of an inhaler, which dispenses the medication in an aerosolized form. For example, the administering means can be a breakable vial, a nasal inhaler, such as a small, squeezable bottle where liquid solution is dispensed in droplets, or the like.

In acute applications, such as a hypertensive crisis, administration of the dynorphin-related compound in accordance with the invention will typically be in substantial dosage, for example, 50 mg/70 kg body weight. It is contemplated such crisis applications will be conducted under the direct control of a physician.

The experiments for which the data is illustrated by FIGS. 1 and 2 were conducted on male Sprague-Dawley rats weighing 250-350 g. Animals were kept under a 12-hour light-dark cycle with food and water available ad libitum. Each rat was used only once. Procedures of infusion of chemicals into the brain and for measurement of heart rate were as reported by Wei, et al., *Life Science,* supra, and Wei, *J. Pharmacol. Exp. Ther.* 21b: 12–18 (1981).

The median effective dose of drugs (ED50) for producing bradycardia was determined in animals anesthetized with 2.5% urethane solution in saline, administered 1.25 g/kg i.p. Drugs, dissolved in distilled water, were injected intravenously into a cannulated femoral vein in a volume of 0.05 ml/100 gm body weight delivered over a period of less than 3 seconds. The pH of the solutions ranged from 5.8 to 6.8 units. The blood pressure was obtained from the left cannulated carotid artery. A Narcobiosystems type 7302 cardiotachometer couple was used to integrate heart rate from the individual oscillations in blood pressure due to the heart beat, and heart rate was recorded on a polygraph recorder. The baseline heart rate ($HR_1$) was defined as the lowest rate observed in the two minutes before drug administration. The magnitude of the change in heart rate was calculated as $[(HR_2-HR_1)/HR_1] \times 100\%$, with the second heart rate ($HR_2$) measured as the lowest rate observed in the three minutes after drug injection.

Saline or distilled water injections produced a 0.9+/−0.6% fall in heart rate. Based on these results, a positive response for bradycardia was defined as a greater than 10% decrease in heart rate. This index was selected because a 10% change could be attributed to the drug's action and not to chance.

The experiment for which data is illustrated by FIG. 3 was conducted on a 4.7 kg cat which was anesthetized with thiopental-chloralose.

Preparation of suitable dynorphin-related compounds for practice of the present invention may be by methods known to the art, with preparation of dynorphin(1-10)-$NH_2$ being illustrative.

EXAMPLE I

Dynorphin(1-10)-$NH_2$ was synthesized on a solid support of Bod-Pro-BHA (Benzyhydrylamine) resin (2 mM/4.5 g of resin). With the Merrifield procedure on a Peninsula manual solid-phase peptide synthesizer, the corresponding Boc-protected amino acids were added respectively onto the Boc-Pro-BHA resin: Arg(Tos), Ile, Arg(Tos), Arg(Tos), Leu, Phe, Gly, Gly and Tyr(o-Br-Z). A 5.0 molar excess of each protected amino acid was used. The success of the coupling reaction was monitored by the semi-quantitative ninhydrin test. The following steps were employed to couple the Boc-protected amino acid to Boc-Pro-BHA resin:

(1) Washing with $CH_2Cl_2$ (3×100 ml)
(2) Prewashing with 33% TFA in $CH_2Cl_2$ with 1% indole (1×100 ml)
(3) Deprotection with 33% TFA in $CH_2Cl_2$ with 1% indole (1×100 ml), 20 in.
(4) Washing with $CH_2Cl_2$ (1×100 ml)
(5) Washing with EtOH (1×100 ml)
(6) Washing with $CH_2Cl_2$ (2×100 ml)
(7) Prewashing with 10% $Et_3N$ in $CH_2Cl_2$ (1×100 ml)
(8) Neutralization with 10% $Et_3N$ in $CH_2Cl_2$ (1×100 ml), 10 min.
(9) Washing with $CH_2Cl_2$ (3×100 ml)
(10) Protected amino acid (5.0 molar excess) in DMF (10 ml) and $CH_2Cl_2$ (50 ml) was added
(11) DCC in $CH_2Cl_2$ (0.5M, 20 ml) was added and the reaction time was up to three hours.
(12) Washing with $CH_2Cl_2$ (3×100 ml)

The resulting protected Boc-Tyr(O-Br-Z)-Gly-Gly-Phe-Leu-Arg(Tos)-Arg(Tos)-Ile-Arg(Tos)-Pro-BHA resin was washed well with 33% TFA in $CH_2Cl_2$, $CH_2Cl_2$ and MeOH respectively. After drying in vacuo overnight, the peptide resin was cleaved by HF (30 ml/g of resin) in the presence of anisole (3 ml/g of resin) for one hour at 0° C. The reaction mixture was dried in vacuo and washed with anhydrous ether. The desired peptide was dissolved in 10% HOAc and the resin was filtered off. The filtrate was lyophilized to give crude dynorphin(1-10)-$NH_2$. This peptide was purified by partition chromatography using n-BuOH:pyridine:$H_2O$ (11:5:3) as eluting solvent and CM ion-exchange chromatography to afford the pure dynorphin(1-10)-$NH_2$.

It is also possible that dynorphin or dynorphin-enkephalin combinations may be used as diagnostic agents for the classification of hypertension and other conditions of autonomic disturbances. Here, dynorphin or its analogs will be administered alone or in combination with an opioid drug and the reactivity, for example, the heart rate change, is used as an index of the functional condition of the person's nervous system.

We claim:

1. A method for treating high blood pressure or disturbances of cardiac function comprising:
administering a therapeutically effective amount of dynorphin(1-13) or dynorphin(1-10).

2. The method as in claim 1 wherein dynorphin(1-10) is amidated.

3. The method as in claim 1 or 2 wherein the administering is at a daily dosage rate of from about 0.14 to about 0.43 mg per kg of body weight.

4. The method as in claim 1 or 2 wherein the administering is at a dosage of at least about 0.70 mg per kg of body weight.

5. The method as in claim 1 or 2 wherein the administering is oral, intranasal, or by injection.

6. The method as in claim 3 wherein the administering is by means of inhalation, and the dynorphin(1-13) or dynorphin(1-10) is in an aerosolized form.

7. The method as in claim 1 or 2 wherein the therapeutically effective dosage lowers such individual's blood pressure by at least about 10%.

* * * * *